(12) United States Patent
Kim

(10) Patent No.: US 8,885,914 B2
(45) Date of Patent: Nov. 11, 2014

(54) APPARATUS AND METHOD FOR REINSPECTING PRESCRIPTION DRUGS

(75) Inventor: Jun-Ho Kim, Daegu (KR)

(73) Assignee: JVM Co., Ltd., Daegu (KR)

( * ) Notice: Subject to any disclaimer, the term of this patent is extended or adjusted under 35 U.S.C. 154(b) by 327 days.

(21) Appl. No.: 13/460,815

(22) Filed: Apr. 30, 2012

(65) Prior Publication Data

US 2012/0280075 A1 Nov. 8, 2012

(30) Foreign Application Priority Data

May 3, 2011 (KR) ........................ 10-2011-0042005

(51) Int. Cl.
- *G06K 9/00* (2006.01)
- *G06K 9/34* (2006.01)
- *G06Q 10/08* (2012.01)
- *G06Q 50/22* (2012.01)

(52) U.S. Cl.
CPC ............... *G06Q 10/08* (2013.01); *G06Q 50/22* (2013.01)
USPC ........... 382/141; 382/143; 382/164; 382/165; 382/170; 382/171

(58) Field of Classification Search
None
See application file for complete search history.

(56) References Cited

U.S. PATENT DOCUMENTS

| 8,582,863 | B2* | 11/2013 | Van Den Brink | 382/140 |
| 2003/0176942 | A1* | 9/2003 | Sleep et al. | 700/213 |
| 2004/0010328 | A1* | 1/2004 | Carson et al. | 700/90 |
| 2007/0000805 | A1* | 1/2007 | Van Den Brink | 206/531 |
| 2010/0085428 | A1* | 4/2010 | Kim | 348/130 |
| 2010/0228562 | A1* | 9/2010 | Luciano et al. | 705/2 |
| 2010/0294927 | A1* | 11/2010 | Nelson et al. | 250/307 |
| 2012/0330684 | A1* | 12/2012 | Jacobs et al. | 705/3 |

\* cited by examiner

*Primary Examiner* — Matthew Bella
*Assistant Examiner* — Jose M Torres
(74) *Attorney, Agent, or Firm* — Novick, Kim & Lee, PLLC; Jae Youn Kim

(57) ABSTRACT

Disclosed are an apparatus and a method for reinspecting a prescription drug, which reinspect the defect state of a defective drug pack after the defect state of an individually packaged drug has been inspected by analyzing the image of the drug. The apparatus includes a drug pack information transceiving module to receive primary inspection data, a drug reinspection controlling module to control a procedure of reinspecting a defect state of a drug pack which has been primarily determined as a defective drug pack, an image processing module to photograph the drug pack, which has been primarily determined as the defective drug pack, and to process an image of the drug pack, and a defect analyzing module to determine a defect state of the drug by analyzing a drug contained in the image of the drug pack provided from the image processing module.

8 Claims, 11 Drawing Sheets

(a)

gray input image (b)

shape of separated drug image (a)

(b)

(c)

(d)

APPARATUS AND METHOD FOR REINSPECTING PRESCRIPTION DRUGS

BACKGROUND OF THE INVENTION

1. Field of the Invention

The present invention relates to a system and a method for reinspecting the defect state of prescription drugs. In more particular, the present invention relates to a system and a method for reinspecting the defect state of a drug pack determined as a defective drug pack after the defect state of the drug pack has been determined by analyzing the image of an individually packaged drug.

2. Description of the Related Art

In general, prescription drugs prepared in a hospital or a pharmacy are individually packaged in the unit of a dose and the packaged prescription drugs are provided to patients on the basis of the duration and frequency for taking the prescription drugs.

Since the prescription drugs are sealed in an individual pack after the preparation of the prescription drugs has been finished, it is difficult to determine if the prescription drugs exactly match with prescription information.

In order to solve the problem, a drug packing paper is made of a transparent material, so that drugs sealed by the packing paper can be easily recognized from the outside.

However, a hospital or a pharmacy, which manages a great amount of prescription drugs, requires great labor force and long inspection time in order to determine the normal preparation state of individually packaged drugs.

In addition, since errors caused due to drugs having the same color or size, or drugs having similar colors or sizes cannot be easily checked, defective prescription drugs may occur. The defective prescription drugs not only degrade the healing effect of patients, but cause fatal injury to the patients.

Therefore, in order to solve the problem, various systems to inspect the defect state of prescription drug packs have been developed. However, when primarily determining the defect state of the prescription drug packs, even through drugs matching with prescription information are exactly packaged, the prescription drug packs are frequently determined as defective drug packs due to the positions of the drugs. Therefore, as the reliability of the primary defect determination is degraded, the reinspection of only the prescription drug packs determined as defective drug packs is required.

In addition, a worker must individually reinspect each of the prescription drug packs primarily determined as defective drug packs. In this case, a long inspection time is required to distinguish the prescription drug packs determined as defective drug packs from many bundles of drug packs. Further, a process of providing drug packs after prescription drugs have been reprepared is not automatically performed.

SUMMARY OF THE INVENTION

Accordingly, the present invention has been made keeping in mind the above problems occurring in the prior art, and an object of the present invention is to provide an apparatus for reinspecting prescription drugs, capable of determining the defect state of prescription drugs by reinspecting only prescription drugs of drug packs determined as defective drug packs based on the inspection data received from a primary drug pack inspection module.

Another object of the present invention is to provide an apparatus for reinspecting prescription drugs, capable of easily searching for prescription information and the result of the primary drug pack inspection by using an ID member formed on a drug pack by additionally including an ID information recognizing module.

Still another object of the present invention is to provide an apparatus for reinspecting prescription drugs, capable of exactly and rapidly providing defective drug packs selected from among a bundle of drug packs which are sequentially linked with each other by additionally including a drug pack transferring module.

Still another object of the present invention is to provide an apparatus for reinspecting prescription drugs, capable of repreparing prescription drugs of a drug pack determined as a defective drug pack by additionally including a defective drug pack correcting module.

Still another object of the present invention is to provide an apparatus for reinspecting prescription drugs, capable of storing information of the reinspection result and managing the information of the correction of a drug pack according the repreparation of the drug pack by additionally including a reinspection information managing module.

Still another object of the present invention is to provide an apparatus for reinspecting prescription drugs, capable of cutting drug packs, which have been completely subject to a reinspection process, according to wards or patients and providing the drug packs to each ward or each patient by additionally including a drug pack providing module.

Still another object of the present invention is to provide an apparatus for reinspecting prescription drugs, capable of acquiring and analyzing only an image of a drug pack determined as a defective drug pack in a primary drug pack inspection module by additionally including an image processing module.

Still another object of the present invention is to provide an apparatus for reinspecting prescription drugs, capable of determining the defect state of a drug pack according to the pattern information of a drug contained in the image of the drug pack by additionally including a defect analyzing module.

Still another object of the present invention is to provide an apparatus for reinspecting prescription drugs, capable of determining the defect state of a prescription drug based on the information of various patterns including the size, the amount, and the appearance of the drug to increase the accuracy for the inspection of the prescription drug.

Still another object of the present invention is to provide a method for reinspecting prescription drugs, capable of determining the defect state of a drug pack by analyzing an image of a defective drug pack.

Still another object of the present invention is to provide a method for reinspecting prescription drugs, capable of reinspecting a drug pack determined as a defective drug pack by recognizing ID information of the drug pack which has been subject to primary drug pack inspection.

Still another object of the present invention is to provide a method for reinspecting prescription drugs, capable of repreparing drugs causing the defect of the drug pack if the drug pack is determined as a defective drug pack even in the reinspection process.

Still another object of the present invention is to provide a method for reinspecting prescription drugs, capable of storing the reinspection result of the drug pack and information of the drug correction of a reprepared drug pack.

Still another object of the present invention is to provide a method for reinspecting prescription drugs, capable of reinspecting a drug pack determined as a defective drug pack by acquiring and analyzing an image of the drug pack to compare the information of the size and the amount of a drug contained in the drug pack with prescription information.

Still another object of the present invention is to provide a method for reinspecting prescription drugs, capable of determining the defect state of a drug by analyzing the size of each drug contained in an image of a drug pack determined as a defective drug pack.

In order to accomplish the above objects, according to one aspect of the present invention, there is provided an apparatus for reinspecting a prescription drug. The apparatus includes a drug pack information transceiving module to receive primary inspection data according to a prescription information and a defect state of the prescription drug, a drug reinspection controlling module connected to the drug pack information transceiving module to control a procedure of reinspecting a defect state of a drug pack which has been primarily determined as a defective drug pack, an image processing module connected to the drug reinspection controlling module to photograph the drug pack, which has been primarily determined as the defective drug pack, and to process an image of the drug pack, and a defect analyzing module connected to the drug reinspection controlling module to determine a defect state of a drug by analyzing the drug contained in the image of the drug pack provided from the image processing module.

According to another aspect of the present invention, there is provided a method for reinspecting a prescription drug. The method includes receiving a result information of primary inspection for a defect of a drug pack from a prescription server and a primary drug pack inspection module through a drug pack information transceiving module, acquiring and analyzing an image of a defective drug pack through an image processing module, and determining a defect state of the drug pack by comparing an inspection result of the primary drug pack inspection module with the image of the defective drug pack through a defect analyzing module.

As described above, according to an apparatus for reinspecting prescription drugs of the present invention, the defect state of prescription drugs is determined by reinspecting only prescription drugs of drug packs determined as defective drug packs based on the inspection data received from a primary drug pack inspection module, thereby improving the efficiency and the reliability when managing prescription drugs.

In addition, according to the apparatus for reinspecting prescription drugs of the present invention, prescription information and the result of the primary drug pack inspection can be easily searched and the drug pack determined as a defective drug pack in the primary drug pack inspection process can be easily provided by using an ID member formed on a drug pack by additionally including an ID information recognizing module.

In addition, according to the apparatus for reinspecting prescription drugs of the present invention, defective drug packs selected from among a bundle of drug packs which are sequentially linked with each other can be exactly and rapidly provided by additionally including a drug pack transferring module.

In addition, according to the apparatus for reinspecting prescription drugs of the present invention, prescription drugs of a drug pack determined as a defective drug pack can be reprepared by additionally including a defective drug pack correcting module.

Further, according to the apparatus for reinspecting prescription drugs of the present invention, information of the reinspection result can be stored and the information of the correction of a drug pack according the repreparation of the drug pack can be managed by additionally including a reinspection information managing module.

In addition, according to the apparatus for reinspecting prescription drugs of the present invention, drug packs, which have been completely subject to a reinspection process, can be cut according to wards or patients and the drug packs can be provided to each ward or each patient by additionally including a drug pack providing module.

In addition, according to the apparatus for reinspecting prescription drugs of the present invention, the height of the worker can be measured.

Further, according to the apparatus for reinspecting prescription drugs of the present invention, only an image of a drug pack determined as a defective drug pack in a primary drug pack inspection module can be acquired and analyzed by additionally including an image processing module.

In addition, according to the apparatus for reinspecting prescription drugs of the present invention, the defect state of a drug pack can be determined according to the pattern information of a drug contained in the image of the drug pack by including a defect analyzing module.

Further, according to the apparatus for reinspecting prescription drugs of the present invention, the defect state of a prescription drug can be determined based on the information of various patterns including the size, the amount, and the appearance of the drug, thereby increasing the accuracy for the inspection of the prescription drug.

In addition, according to a method for reinspecting prescription drugs of the present invention, the defect state of a drug pack can be determined by analyzing an image of a defective drug pack.

Further, according to the method for reinspecting prescription drugs of the present invention, a drug pack determined as a defective drug pack can be reinspected by recognizing ID information of the drug pack which has been subject to primary drug pack inspection.

Additionally, according to the method for reinspecting prescription drugs of the present invention, drugs causing the defect of the drug pack can be reprepared if the drug pack is determined as a defective drug pack even in the reinspection process.

Additionally, according to the method for reinspecting prescription drugs of the present invention, the reinspection result of the drug pack and information of the drug correction of a reprepared drug pack can be stored.

Besides, according to the method for reinspecting prescription drugs of the present invention, the defect state of a drug pack determined as a defective drug pack can be reinspected by acquiring and analyzing an image of the drug pack to compare the information of the size and the amount of a drug contained in the drug pack with prescription information.

In addition, according to the method for reinspecting prescription drugs of the present invention, the defect state of a drug can be determined by analyzing the size of each drug contained in an image of a drug pack determined as a defective drug pack.

DETAILED DESCRIPTION OF THE INVENTION

Hereinafter, an apparatus and a method for reinspecting prescription drugs according to the present invention will be described with reference to accompanying drawings.

Figure 1:
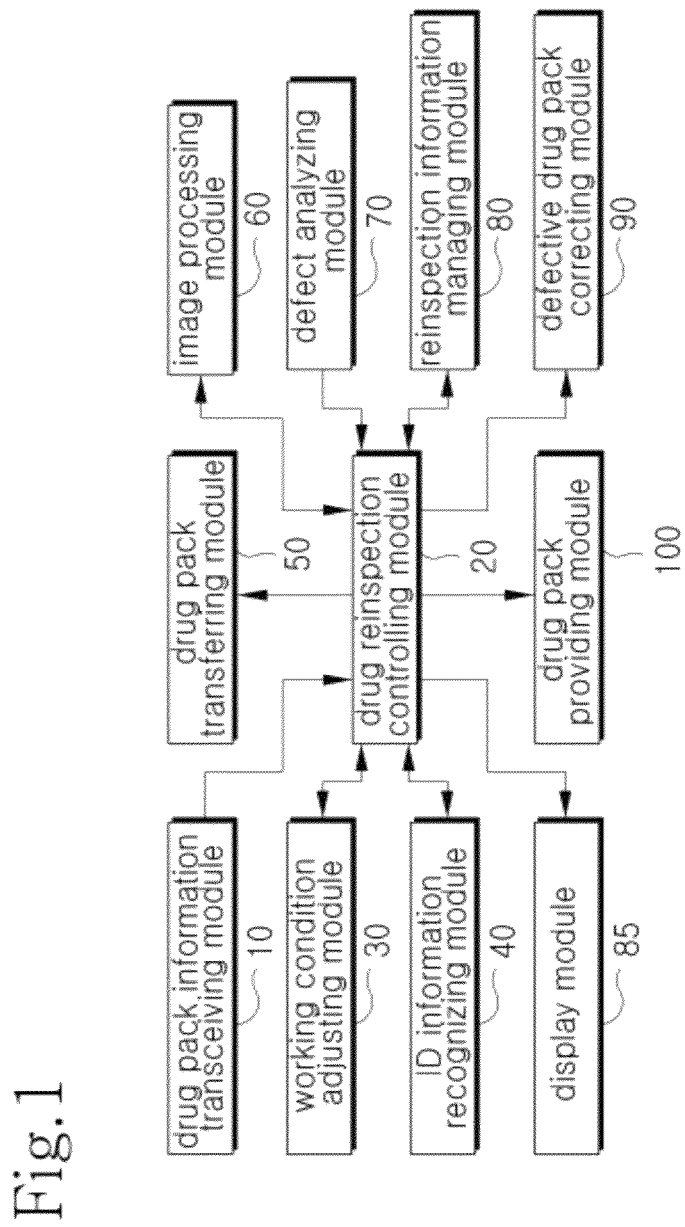
FIG. 1 is a block diagram showing the whole structure of an apparatus for reinspecting prescription drugs according to the present invention.

FIG. 1 is a block diagram showing the whole structure of an apparatus for reinspecting prescription drugs according to the present invention. The apparatus for reinspecting prescription drugs includes a drug pack information transceiving module 10, a drug reinspection controlling module 20, a working condition adjusting module 30, an ID information recognizing module 40, a drug pack transferring module 50, an image processing module 60, a defect analyzing module 70, a reinspection information managing module 80, a display module 85, a defective drug pack correcting module 90, and a drug pack providing module 100.

The drug pack information transceiving module 10 receives primary inspection data according to prescription information and the defect state of the prescription drugs.

The drug pack information transceiving module 10 according to the present invention is connected to a prescription information managing server to search for the prescription information, and connected to a primary drug pack inspection module to receive the information of a drug pack, which has been determined as a defective drug pack in the primary drug pack inspection, and the information of a drug pack ID. In addition, the drug pack information transceiving module 10 transfers the information of the reinspection of the drug pack to the outside after the prescription drug pack has been reinspected.

The drug reinspection controlling module 20 is connected to the drug pack information transceiving module 10 to control a procedure of reinspecting the defect state of the drug pack, which has been determined as a defective drug pack in the primary drug pack inspection.

Figure 2:
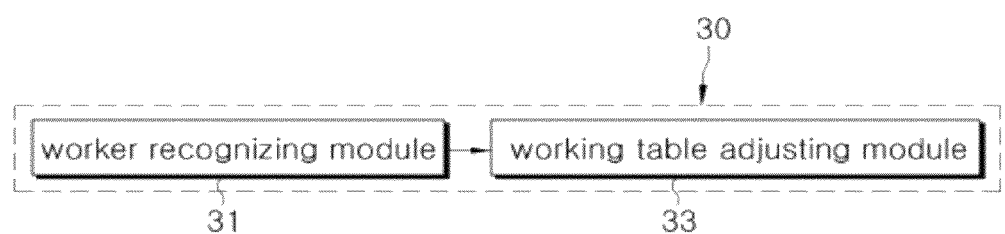
FIG. 2 is a detailed block diagram showing a working condition adjusting module in the apparatus for reinspecting prescription drugs according to the present invention.

The working condition adjusting module 30 is connected to the drug reinspection controlling module 20 to adjust a working condition for the inspection of the drug pack. As shown in FIG. 2, the working condition adjusting module 30 includes a worker recognizing module 31 and a working table adjusting module 33.

The worker recognizing module 31 is connected to the drug reinspection controlling module 20 to measure the height of a worker in the inspection of the drug pack, and the working table adjusting module 33 is connected to the worker recognizing module 31 to adjust the height of the working table according to the height of the worker recognized by the worker recognizing module 31.

The working condition adjusting module 30 according to the present invention is provided to adjust the height of the working table based on the height of the worker, so that the inspection efficiency for the drug pack by the worker can be improved.

The ID information recognizing module 40 is connected to the drug reinspection controlling module 20 to recognize ID information of an ID member formed on a drug pack. In detail, the ID information recognizing module 40 recognizes the ID information of the ID member attached to the drug pack after a primary drug pack inspection has been finished, or recognizes the ID information of the ID member printed on the drug pack in an initial packaging work. The ID information contains the information of each drug and the defect state of the drug.

Preferably, the ID information recognizing module 40 according to the present invention further includes an auxiliary ID information recognizing module 45 to recognize ID information of an individual drug pack instead of a bundle of drug packs in addition to a device to recognize the ID information of each drug pack when a bundle of drug packs are transferred.

In other words, the auxiliary ID information recognizing module 45 is additionally provided to manually recognize an individual drug pack which cannot be transferred through the drug pack transferring module 50, so that the preparation defect of prescription drugs can be reinspected.

The drug pack transferring module 50 is connected to the drug reinspection controlling module 20 to transfer drug packs, which have been primarily determined as defective packs among a bundle of drug packs subject to the primary drug pack inspection, to the image processing module 60.

In addition, the drug pack transferring module 50 according to the present invention includes at least two drug pack bobbin devices 51, and transfer rollers 52 and 53 including an elastic material are interposed between the two drug pack bobbin devices 51.

In other words, a bundle of drug packs are wound at a high speed through interaction between the drug pack bobbin devices until the drug pack primarily determined as the defective drug pack comes, and all drug packs which have been subject to a defect state reinspection process are wound.

As the drug packs primarily determined as defective drug packs due to the overlap of the positions of the drugs are shaken through the winding or releasing operation of a bundle of the drug packs by the drug pack bobbin devices 51, the positions of the drugs may be rearranged and the drugs may be inspected.

A defective drug pack can be easily recognized as the primary drug pack inspection is performed based on the ID information recognized in the ID information recognizing module 40 according to the present invention, and only the drug packs primarily determined as a defective pack are provided by the drug pack transferring module 50 for the reinspection purpose, so that the reinspection time of the drug pack can be reduced.

In addition, preferably, the drug pack transferring module 50 according to the present invention further includes an emergency stop button 54 to stop the operation of the drug pack bobbin device 51 in the emergency situation.

Figure 3:
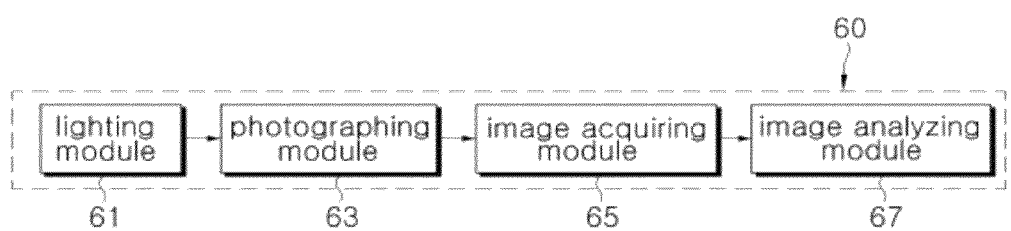
FIG. 3 is a detailed block diagram showing an image processing module in the apparatus for reinspecting prescription drugs according to the present invention.

The image processing module 60 is connected to the drug reinspection controlling module 20 to photograph a drug pack, which has been determined as a defective drug pack in the primary drug pack inspection, and to process the image of the drug pack. As shown in FIG. 3, the image processing module 60 includes a lighting module 61, a photographing module 63, an image acquiring module 65, and an image analyzing module 67.

The photographing module 63 photographs the drug pack which has been primarily determined as a defective drug pack, and the image acquiring module 65 is connected to the photographing module 63 to collect image frames obtained through the photographing operation.

The image analyzing module 67 is connected to the image acquiring module 65 to analyze a drug image and extract the pattern information of each drug, and the lighting module 61 adjusts the photographing mode of the photographing module 63 for drug packing paper and drugs contained in a drug pack.

Hereinafter, the operation of the image processing module 60 according to the present invention will be described in detail.

Figure 4:
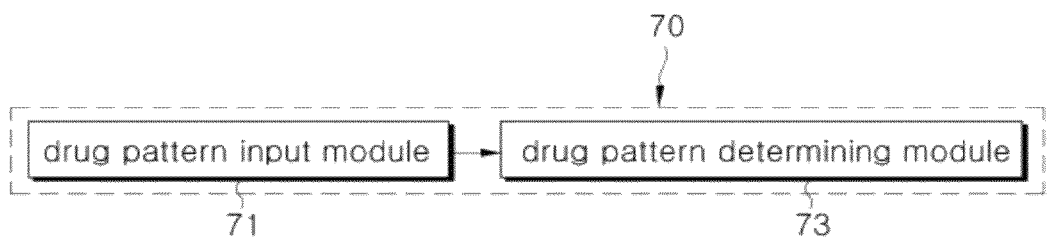
FIG. 4 is a detailed block diagram showing a defect analyzing module in the apparatus for reinspecting prescription drugs according to the present invention.

The defect analyzing module 70 is connected to the drug reinspection controlling module 20 to analyze the drug of a drug pack image provided from the image processing module 60 so that the defect state of the drug can be determined. As shown in FIG. 4, the defect analyzing module 70 includes a drug pattern input module 71 and a drug pattern determining module 73.

The drug pattern input module 71 inputs the basic information of an individual drug and the pattern information of a drug contained in the image of the photographed drug appearance. The drug pattern determining module 73 is connected to the drug pattern input module 71 to compare the pattern information of the drug according to the prescription information with the pattern information of the drug stored in the drug pattern storing module and determine if the pattern information of the drug according to the prescription information matches with the pattern information of the drug stored in the drug pattern storing module.

The pattern information of the drug according to the present invention preferably includes at least one of the size, the amount, the appearance, the color, the symbol mark, the weight, and the thickness of the drug.

The operation of the defect analyzing module 70 according to the present invention will be described below together with the image processing module 60.

The reinspection information managing module 80 is connected to the drug reinspection controlling module 20 to store the information of the reinspection result and manage the correction information of the reprepared drug pack.

The information stored in the reinspection information managing module 80 includes prescription information of drugs, the information of the drugs, the information of drug correction, the information of a worker, and the information of a working time which are searched when the drugs are reinspected.

The display module 85 is connected to the drug reinspection controlling module 20 to display the reinspection procedure of a drug to the outside, so that a worker can recognize the procedure of analyzing a drug pack image and prescription information in the image processing module 60 and the defect analyzing module 70.

The defective drug pack correcting module 90 is connected to the drug reinspection controlling module 20 to reprepare drugs in a drug pack, which has been primarily determined as a defective drug pack, based on the defect information if the drug pack is determined as a defective drug pack after the drug pack has been reinspected. In detail, the defective drug pack correcting module 90 according to the present invention is preferably realized through a device in which a drug pack opening member, a drug supplying module to supply a drug according to the prescription information, and a member of sealing the open drug pack are integrally formed with each other.

The drug pack providing module 100 is connected to the drug reinspection controlling module 20 to provide drug packs by cutting the drug packs according to the information of the wards and patients after the reinspection process has been finished, or by winding a bundle of the drug packs similarly to the case of providing drug packs when the reinspection of the drug packs is started.

Figure 11:
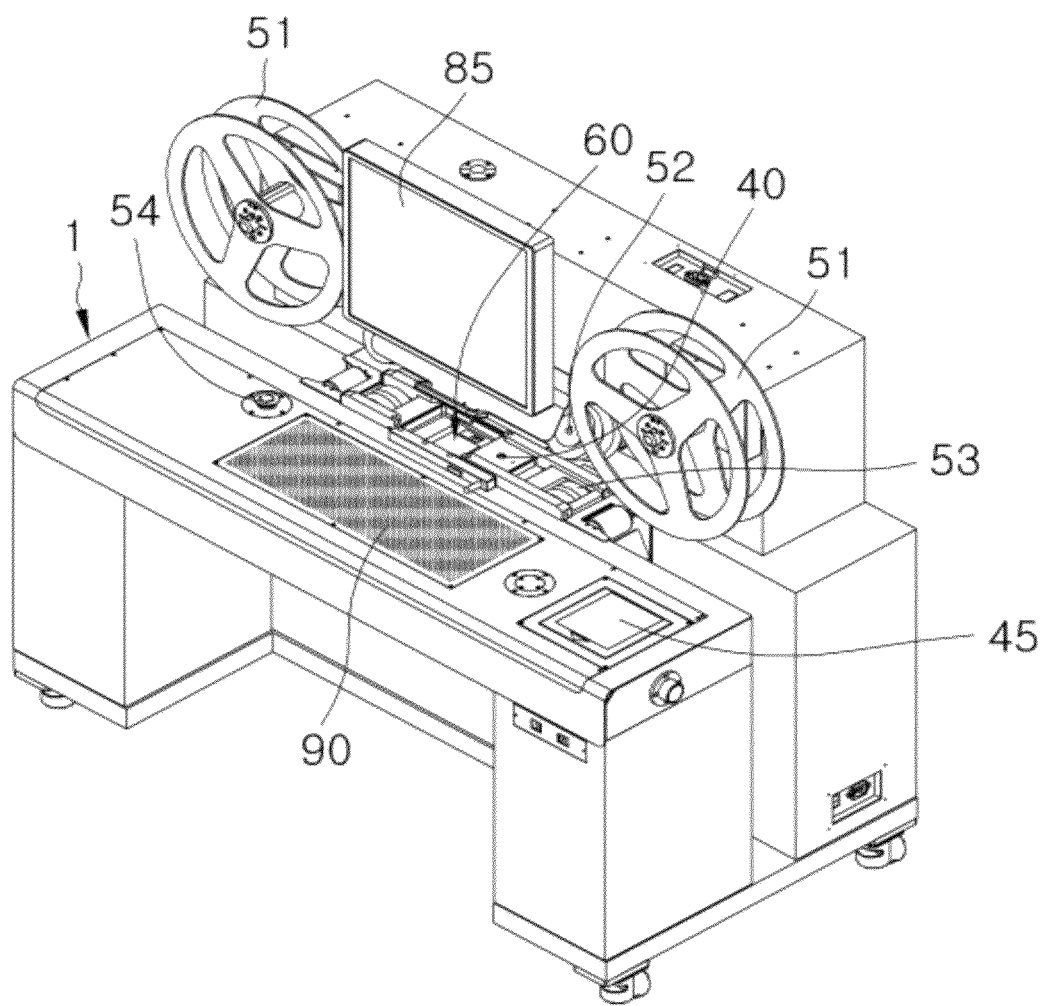
FIG. 11 is a view showing an apparatus for reinspecting prescription drugs according to one embodiment of the present invention.

FIG. 11 is a view showing an apparatus for reinspecting prescription drugs according to one embodiment of the present invention. As shown in FIG. 11, the display module 85 is provided to display the reinspection situation to the outside, the drug pack bobbin devices 51 are provided at both sides of the display module 85, and the transfer rollers 52 and 53 are provided between the drug pack bobbin devices 51.

The image processing module 60 is provided below the transfer rollers 52 and 53 to photograph the prescription drug pack, which is being transferred, and process the image of the photographed prescription drug pack. The ID information recognizing module 40 is provided on the transfer line of the prescription drug pack to recognize the ID information formed on the prescription drug pack.

In addition, the defective drug pack correcting module 90 is provided on the working table 1 to correctly prepare the prescription drug pack determined as a defective drug pack.

In addition, the auxiliary ID information recognizing module 45 is provided at one side of the working table 1 to recognize the ID information of an individual drug pack instead of a bundle of drug packs.

As described above, according to the apparatus for reinspecting prescription drugs of the present invention, only drugs contained in the drug pack determined as a defective drug pack are reinspected based on the inspection data received from the primary drug pack inspection module to determine the defect state of the drug pack, so that the efficiency and the reliability of the prescription drug management can be improved.

Hereinafter, the method for reinspecting the prescription drugs according to the present invention will be described.

Figure 5:
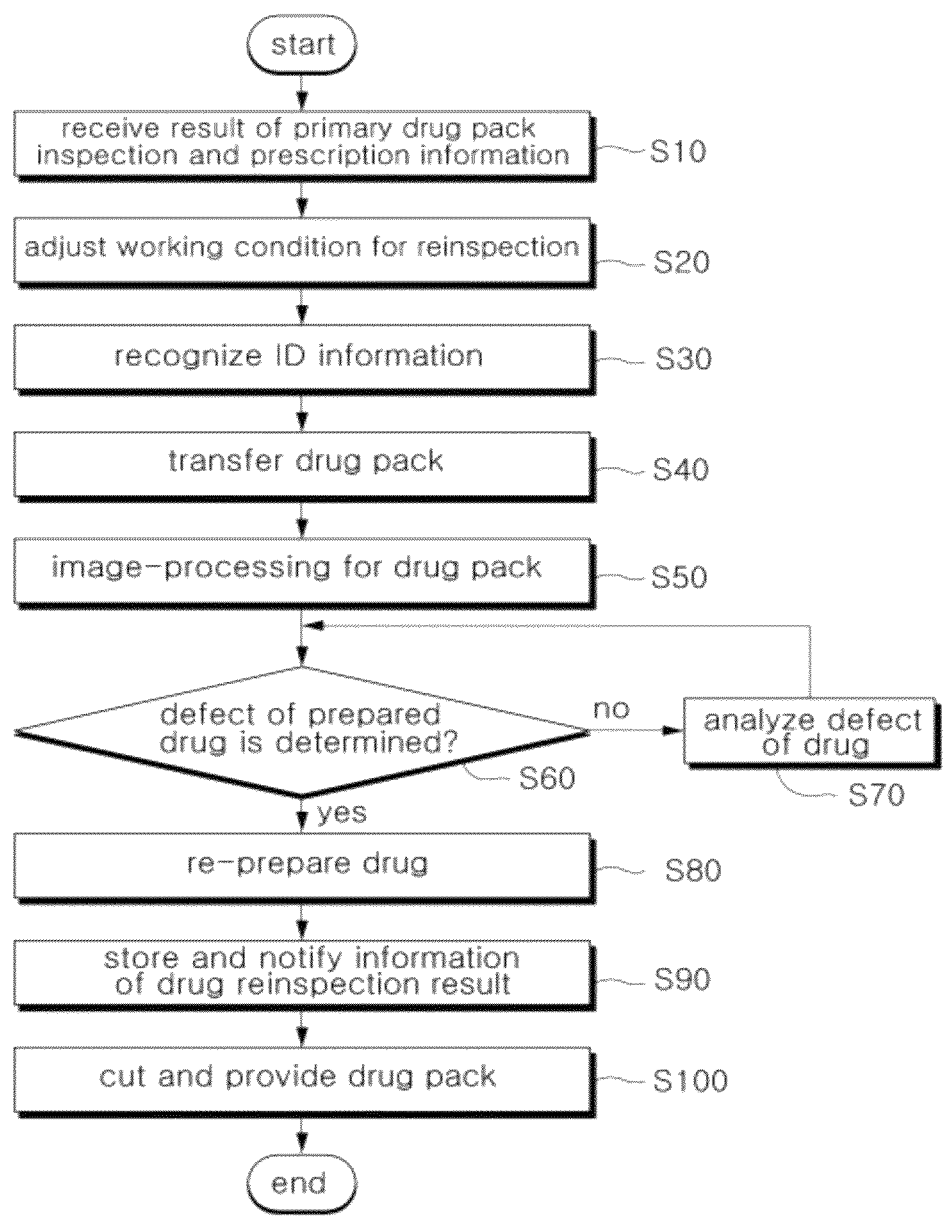
FIG. 5 is a flowchart showing a method for reinspecting prescription drugs according to the present invention.

FIG. 5 is a flowchart showing a method for reinspecting prescription drugs according to the present invention. The drug pack information transceiving module 10 receives the result information of primary inspection for the defects of a drug pack from a prescription server and the primary drug pack inspection module (step S10).

In other words, step S10 is to receive the prescription information of a drug from the prescription server and receives the result information of the primary inspection for the defects of the drug pack from the primary drug pack inspection module.

Figure 6:
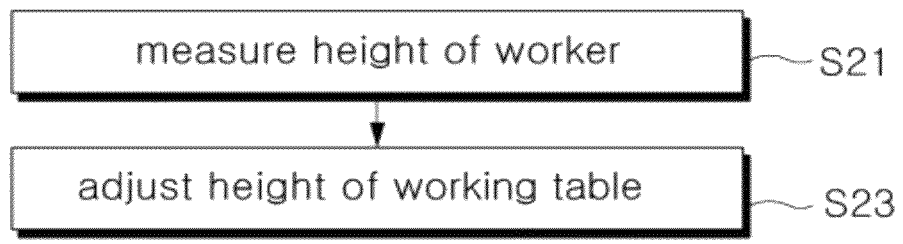
FIG. 6 is a detailed flowchart showing step S20 in the method for reinspecting prescription drugs according to the present invention.

Next, the working condition adjusting module 30 adjusts a working condition for the reinspection of the drug pack (step S20). As shown in FIG. 6, step S20 includes a step of measuring the height of a worker by using the worker recognizing module 31 (step S21) and a step of adjusting the height of the working table based on the height of the worker by using the working table adjusting module 33 (step S23).

Thereafter, the ID information recognizing module 40 recognizes the ID information of an ID member formed on the drug pack (step S30).

In other words, step S30 is to recognize the ID member attached to the drug pack or formed on the drug pack after the inspection of the drug pack has been finished by the primary drug pack inspection module. Accordingly, the existence of defective drug packs can be checked and only the drug pack determined as a defective drug pack in the primary drug pack inspection can be reinspected, by performing step S30.

Next, the drug pack transferring module 50 transfers the drug pack determined as a defective drug pack (step S40).

In other words, step S40 is to provide the drug pack determined as a defective drug pack in the primary drug pack inspection at a high speed by using the ID information recognized by the ID information recognizing module 40 in step S30.

Next, the image processing module 60 acquires and analyzes the image of the defective drug pack (step S50).

Figure 7:
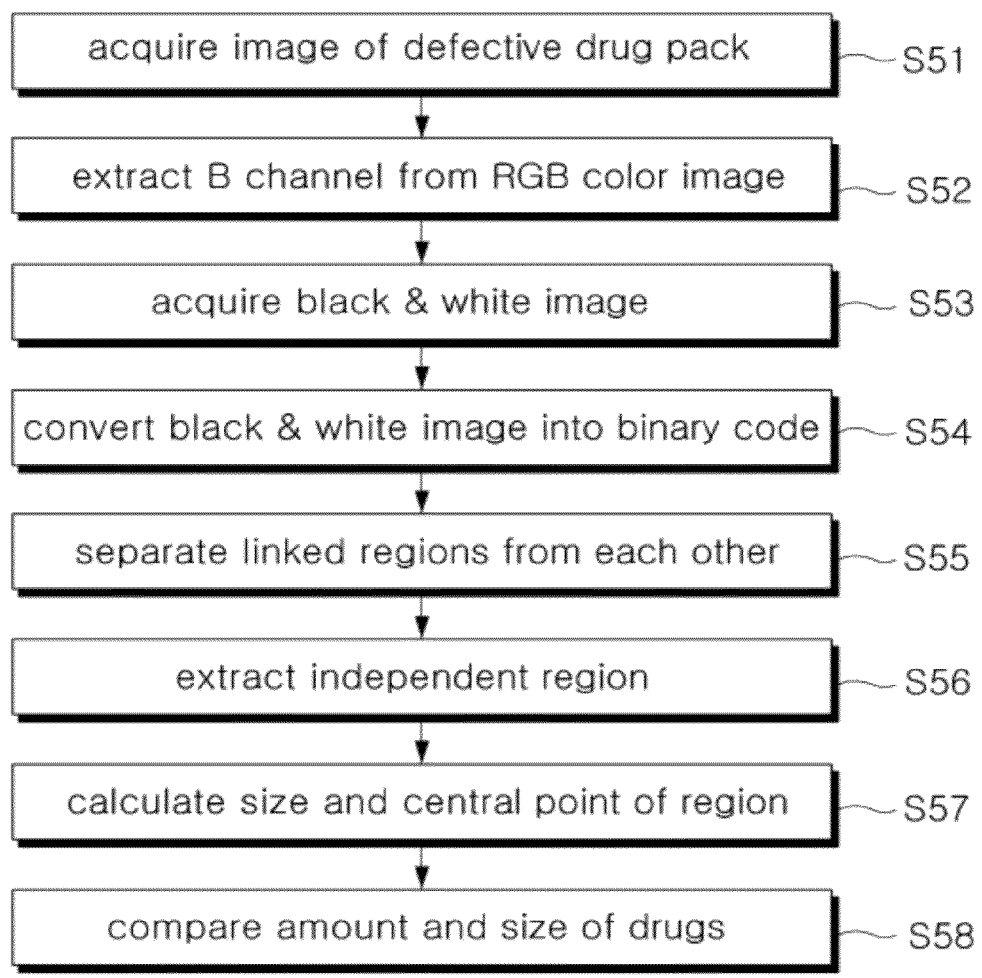
FIG. 7 is a detailed flowchart showing step S50 in the method for reinspecting prescription drugs according to the present invention.

FIG. 7 is a detailed flowchart showing step S50 in the method for reinspecting prescription drugs according to the present invention. First, the photographing module 63 takes an RGB color image of the defective drug pack, and the image acquiring module 65 acquires the image frame of the RGB color image (step S51).

Next, a B channel is extracted from the RGB color image (step S52), and the black & white image of the prescription drug is acquired (step S53).

In this case, both of a color image and a black & white image can be acquired through one photographing module by adjusting the lighting module 61.

Subsequently, the black & white image is converted into a binary image by using a critical value (step S54).

In step S54, the critical value is a reference pixel value used to convert the black & white image into a binary image.

Figure 8:
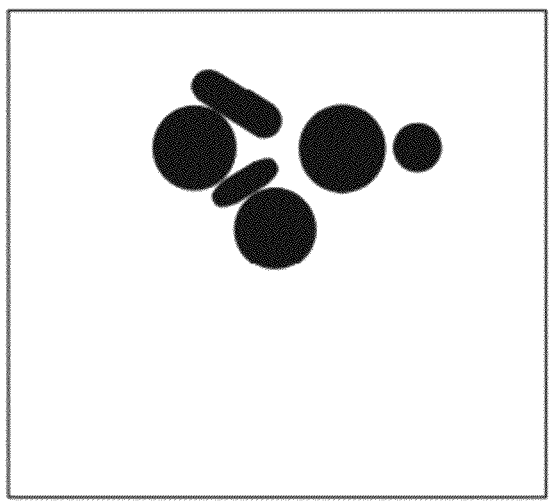
FIGS. 8(a) and 8(b) are views showing step S50 in the method for reinspecting prescription drugs according to one embodiment of the present invention.
Figure 8:
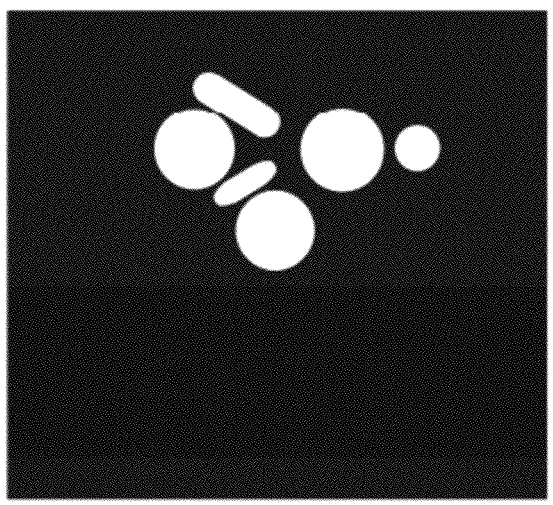

FIG. 8(a) is a view showing a black & white image of the prescription drug in step S53 according to one embodiment of the present invention.

Next, linked regions of drugs are separated from each other in the binary image (step S55).

According to the embodiment of the present invention, step S55 is performed by extracting a circular image in a predetermined section from the corner center of the binary image, and measuring the area of the image and the angle of a separation line to determine the contact corner of drugs.

Thereafter, the independent region of each drug is extracted (step S56).

FIG. 8(b) is a view showing an image of the independent regions of the prescription drug according to one embodiment of the present invention.

Next, the size, the central point, and the number of the independent regions are calculated (step S57).

Thereafter, it is determined if the size and the amount of drugs obtained through the image analysis in step S50 match with the size and the amount of drugs contained in the prescription information (step S58).

Next, the prescription drugs are determined as defective drugs (step S60).

If the size and the amount of the prescription drugs obtained through the image analysis in step S50 do not match with the size and the amount of the prescription drugs contained in the prescription information so that the prescription drugs are determined as defective drugs in step S60, prescription drugs are reprepared (step S80).

If the size and the amount of the prescription drugs obtained through the image analysis in step S50 match with the size and the amount of the prescription drugs contained in the prescription information so that the prescription drugs are not determined as defective drugs in step S60, the defect state of the drug pack is determined by comparing the inspection result of the primary drug pack inspection module and the image of the defective drug pack through the defect analyzing module 70 (step S70).

Figure 9:
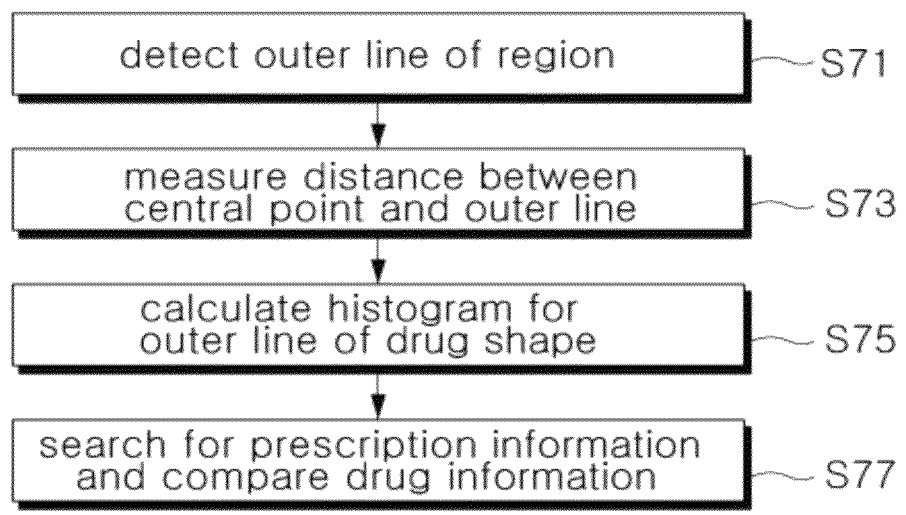
FIG. 9 is a detailed flowchart showing step S70 in the method for reinspecting prescription drugs according to the present invention.

FIG. 9 is a detailed flowchart showing step S70 according to the present invention, and the outer line of the independent region of the drug is detected (step S71).

Figure 10:
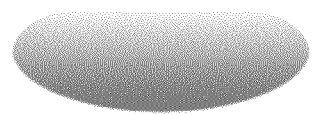
FIGS. 10(a) to 10(d) schematically illustrate views showing step S70 in the method for reinspecting prescription drugs according to the present invention.
Figure 10:
Figure 10:
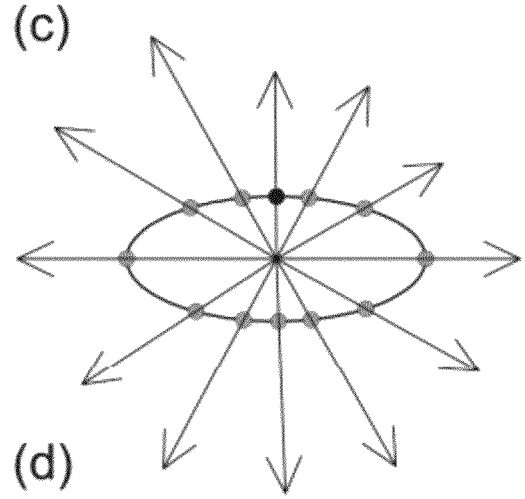
Figure 10:
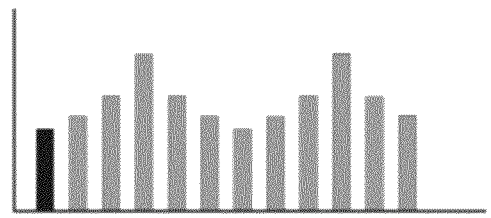

FIGS. 10a to 10d are views showing the images obtained by analyzing a drug pattern through the detailed steps of step S70 according to one embodiment of the present invention, and step S71 is performed so that the outer line is detected from the independent region as shown in FIG. 10(a) like the image shown in FIG. 10(b).

Next, as shown in FIG. 10(c), the distance between the outer line of the drug and the central point of the drug is measured (step S73).

Thereafter, as shown in FIG. 10(d), the histogram of the outer line of a drug appearance is calculated (step S75).

Subsequently, the histogram information of the drug is compared with the drug information of the prescription information to determine if the histogram information of the drug matches with the drug information of the prescription information (step S77).

Next, it is determined if an oval drug according to the embodiment of the present invention matches with a drug stored in the drug pattern storing module, and the information of the drug matches with the prescription information (step S60).

If it is determined in step S60 that the histogram information of the drug is different from the drug information of the prescription information, a drug is reprepared (step S80), and the information of the reinspection result is stored and notified to a pharmacy management server or the worker (step S90).

Next, the drug pack providing module cuts drug packs or winds a bundle of drug packs according to wards or patients and provides the drug packs to each ward or each patient (step S100).

According to the method for reinspecting prescription drugs of the present invention, the image of a drug pack determined as a defective drug pack in the primary inspection of the drug pack is analyzed, so that the defect state of the drug pack can be quickly determined.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method for reinspecting a prescription drug, the method comprising:
   receiving a result information of primary inspection for a defect of a drug pack from a prescription server and a primary drug pack inspection module through a drug pack information transceiving module;
   acquiring and analyzing an image of a defective drug pack through an image processing module; and
   determining a defect state of the drug pack by comparing an inspection result of the primary drug pack inspection module with the image of the defective drug pack through a defect analyzing module, wherein the acquiring and analyzing of the image of the defective drug pack comprises:
photographing the prescription drug in a form of an RGB image and collecting the RGB image;
extracting a B channel from a collected drug image;
acquiring a black & white image of the prescription drug;
inputting the black & white image of the prescription drug;
creating a binary image by using a critical value;
separating linked drug regions from each other in the binary image;
extracting an independent region of each drug;
extracting a size, a central point, and an amount of the independent region; and
determining if a size and an amount of the photographed prescription drug matches with a size and an amount of a drug according to a prescription information.

2. The method of claim 1, further comprising:
recognizing an ID information of an ID member formed on the drug pack through an ID information recognizing module; and
transferring the defective drug pack through a drug pack transferring module, after receiving the result information of the primary inspection for the defect of the drug pack.

3. The method of claim 1, wherein, in the determining of the defect state of the drug pack, if the drug pack is determined as the defective drug pack, the defective drug pack is reprepared through a drug pack correcting module.

4. The method of claim 1, further comprising:
storing a result of a reinspection operation for the drug pack through a reinspection information managing module; and
cutting and providing drug packs according to wards or patients through a drug pack providing module, after determining the defect state of the drug pack.

5. A method for reinspecting a prescription drug, the method comprising:
receiving a result information of primary inspection for a defect of a drug pack from a prescription server and a primary drug pack inspection module through a drug pack information transceiving module;
acquiring and analyzing an image of a defective drug pack through an image processing module; and
determining a defect state of the drug pack by comparing an inspection result of the primary drug pack inspection module with the image of the defective drug pack through a defect analyzing module,
wherein the determining of the defect state of the drug pack comprises:
detecting an outer line of an independent region of an image of a drug;
measuring a distance between the outer line of the drug and a central point of the drug;
calculating a histogram of an outer line of a drug shape; and
determining if a histogram information of the drug matches with a drug information of a prescription information.

6. The method of claim 5, further comprising:
recognizing an ID information of an ID member formed on the drug pack through an ID information recognizing module; and
transferring the defective drug pack through a drug pack transferring module, after receiving the result information of the primary inspection for the defect of the drug pack.

7. The method of claim 5, wherein, in the determining of the defect state of the drug pack, if the drug pack is determined as the defective drug pack, the defective drug pack is reprepared through a drug pack correcting module.

8. The method of claim 5, further comprising:
storing a result of a reinspection operation for the drug pack through a reinspection information managing module; and
cutting and providing drug packs according to wards or patients through a drug pack providing module,
after determining the defect state of the drug pack.

* * * * *